United States Patent [19]

Stindl et al.

[11] Patent Number: 4,918,065

[45] Date of Patent: Apr. 17, 1990

[54] CORTICOID-CONTAINING PREPARATION FOR TOPICAL APPLICATION

[75] Inventors: Wolfgang Stindl, Eisenstadt, Austria; Ingfried Zimmerman, Berlin; Renate Reckers, Berlin; Hans Wendt; Rainold Arndt, both of Berlin, all of Fed. Rep. of Germany

[73] Assignee: Schering Aktiengesellschaft, Berlin and Bergkamen, Fed. Rep. of Germany

[21] Appl. No.: 258,055

[22] Filed: Oct. 17, 1988

Related U.S. Application Data

[63] Continuation of Ser. No. 937,282, Dec. 3, 1986, which is a continuation of Ser. No. 835,490, Mar. 3, 1986, which is a continuation of Ser. No. 734,724, May 16, 1985, which is a continuation of Ser. No. 511,404, Jul. 7, 1983 all abandoned.

[30] Foreign Application Priority Data

Jul. 7, 1982 [DE] Fed. Rep. of Germany ....... 3225848

[51] Int. Cl.$^4$ .............................................. A61K 31/56
[52] U.S. Cl. ..................................... 514/179; 514/180
[58] Field of Search ........................ 518/169, 179, 180

[56] References Cited

U.S. PATENT DOCUMENTS 4,115,313 9/1978 Lyon et al. ............................ 424/57
4,284,630 8/1981 Yu et al. ............................... 514/179

FOREIGN PATENT DOCUMENTS 1949740 7/1970 Fed. Rep. of Germany .

OTHER PUBLICATIONS

Die Emulsionen in der Hauttherapie, S. Hirzel Verlag Stuttgart, p. 223, 1951.
Brunegger et al., Sci. Pharm. 53, 1985, pp. 223–236.
"Vivoane" Brochure, pp. 3, and 6–13.
Test Report I, AT-2071/81.

*Primary Examiner*—Joseph A. Lipovsky
*Attorney, Agent, or Firm*—Millen, White & Zelano

[57] ABSTRACT

A corticoid-containing pharmaceutical preparation adapted for topical application, comprising 0.005–2% by weight of a corticoid having antiinflammatory activity, a fatty phase, an aqueous phase, an emulsifier, a preservative, and, optionally, a fragrant substance, or an additional hydrophilic or lipophilic cosmetically active ingredients, wherein the fatty phase, and the aqueous phase are present in the form of a dispersed mixture of an oil/water emulsifier and a preservative, and a water-/oil emulsion containing a water/oil emulsifier, the particle size of the inner phase of the emulsions being 2–50 μm.

15 Claims, No Drawings

CORTICOID-CONTAINING PREPARATION FOR TOPICAL APPLICATION

CROSS REFERENCE TO RELATED APPLICATIONS

This application is a continuation, of application Ser. No. 06/937,282, filed Dec. 3, 1986, which is a continuation of Ser. No. 06/835,490, filed Mar. 3, 1986, which is a continuation of Ser. No. 06/734,724, filed May 16, 1985, which is a continuation of Ser. No. 06/511,404, filed Jul. 7, 1983, all now abandoned.

SUMMARY OF THE INVENTION

It is an object of this invention to provide improved topical corticoidal preparations.

Upon further study of the specification and appended claims, further objects and advantages of this invention will become apparent to those skilled in the art.

The objects of this invention have been achieved by providing corticoid-containing preparations for topical application containing 0.005-2% by weight of a corticoid having antiinflammatory activity, optional additional hydrophilic and/or lipophilic active ingredients (e.g., pharmacologically or cosmetically active), as well as a fatty phase, an aqueous phase, emulsifiers, preservatives, as well as optional fragrant substances, wherein the preparation contains the corticoid, the hydrophilic and/or lipophilic active ingredients, the fatty phase, and the aqueous phase in the form of an extremely finely dispersed mixture of an oil/water emulsion containing an oil/water emulsifier and preservatives, and contains a water/oil emulsion containing a water/oil emulsifier.

Suitable corticoids include those of Formula I

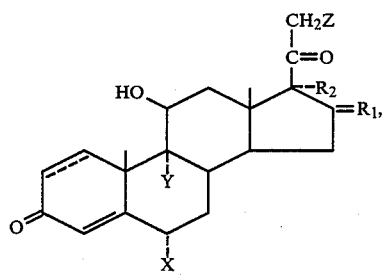

wherein
--is a single bond or a double bond
X is hydrogen, fluorine, or methyl,
Y is hydrogen, fluorine, or chlorine, and
Z is hydroxy, alkanoyloxy of 2-6 carbon atoms, benzoyloxy, or chlorine,
$R_1$ and $R_2$ jointly represent an isopropylidenedioxy group or
$R_1$ is two hydrogen atoms, a hydrogen atom and a hydroxy group, a methylene group, or a hydrogen atom and a methyl group, and
$R_2$ is hydrogen, hydroxy, alkanoyloxy of 2-6 carbon atoms, ($C_{1-4}$-alkoxy)methyl, or benzoyloxy.

These include those of Formula Ia

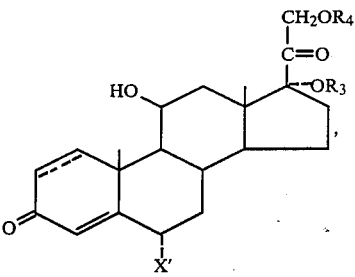

wherein
-- is a single bond or a double bond,
X' is hydrogen or methyl, and
$R_3$ and $R_4$, being identical or different, are hydrogen, alkanoyl of 2-6 carbon atoms, ($C_{1-4}$-alkoxy)methyl or benzoyl;

Formula Ib

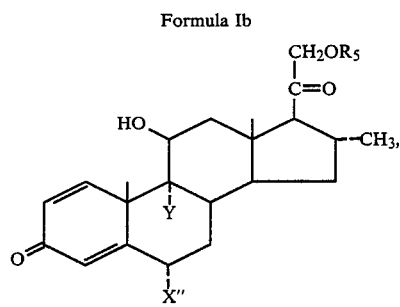

wherein
Y is a defined for Formula I
X" is hydrogen or fluorine, and
$R_5$ is hydrogen, alkanoyl of 2-6 carbon atoms, or benzoyl;

Formula Ic

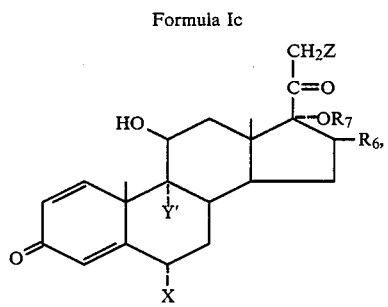

wherein
X and Z are as defined for Formula I
$R_6$ is hydrogen, methylene, or methyl and
$R_7$ is hydrogen, alkanoyl of 2-6 carbon atoms, or benzoyl;

Formula Id

-continued

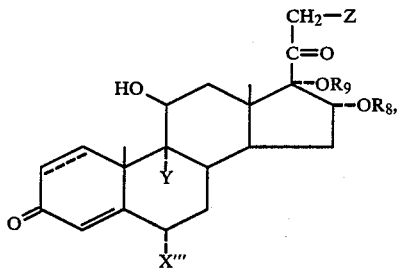

Id wherein
—, Z, and Y are as defined for Formula I
X''' is hydrogen or fluorine, and
R$_8$ and R$_9$ each represents hydrogen or collectively represent isopropylidene.

Preferably, the particle size of the emulsions is 2–50 μm. Further preferably, a process for the production of the corticoid-containing preparation involves preparing an oil/water emulsion from a fatty phase, aqueous phase, oil/water emulsifier, and preservative, and a water/oil emulsion from a fatty phase, aqueous phase, and water/oil emulsifier; intimately intermixing the two emulsions with agitation, adding hydrophilic and/or lipophilic active agents, under a vacuum at a temperature of 20° to 40° C.; and thereupon combining the resultant, finely dispersed mixture with the micronized corticoid and with fragrant substances.

DETAILED DISCUSSION

Basically, all corticoids having antiinflammatory activity are equivalents for the production of the corticoid-containing preparations of this invention. However, the corticoids mentioned above are preferred.

Corticoids of Formula Ia suitable for the production of the corticoid-containing preparations of this invention include hydrocortisone, prednisolone, 6α-methylhydrocortisone, 6α-methylprednisolone, and the esters or acetals thereof, e.g., hydrocortisone 21-acetate, hydrocortisone 17-butyrate, hydrocortisone 17-valerate, prednisolone 21-acetate, prednisolone 17-valerate, 6α-methylhydrocortisone 21-acetate, 6α-methylprednisolone 21-acetate, 6α-methylhydrocortisone 17-butyrate-21-acetate, 6α-methylprednisolone 21-acetate-17-propionate, 6α-methylhydrocortisone 17,21-dipropionate, or 21-acetoxy-17α-ethoxymethoxy-11β-hydroxy-1,4-pregnadiene-3,20-dione.

Corticoids of Formula Ib suitable for producing the corticoid-containing preparations of this invention include, for example, fluocortolone, clocortolone, diflucortolone, desoximetasone, and the esters thereof, e.g., fluocortolone 21-acetate, fluocortolone 21-caproate, fluocortolone 21-trimethylacetate, clocortolone 21-caproate, clocortolone 21-trimethylacetate, and diflucortolone 21-valerate.

Corticoids of Formula Ic suitable for the production of the corticoid-containing preparations of this invention include, for example, betamethasone, beclomethasone, fluprednylidene, clobetasol, dexamethasone, flumethasone, 9-chloroprednisolone, and the esters thereof, e.g., betamethasone 17-valerate, betamethasone 17-benzoate, betamethasone 17,21-dipropionate, beclomethasone 17,21-dipropionate, fluprednylidene 21-acetate, clobetasol 17-propionate, flumethasone 21-trimethylacetate, 9-chloroprednisolone 21-acetate-17-propionate, and 9-chloroprednisolone 17-butyrate-21-propionate.

Corticoids of Formula Id suitable for the production of the corticoid-containing preparations of this invention include, for example, triamcinolone, triamcinolone acetamide, halcinonide, fluocinolone, fluocinolone acetonide, desonide, fludroxycortide, and the esters thereof, such as, for example, fluocinonide.

However, likewise suited for the production of the corticoid-containing preparations of this invention are those antiinflammatorily active corticoids not covered by these structural formulae, e.g., of Formula I. Such corticoids include, for example, those differing from the corticoids of Formula I by carrying, in place of the grouping $$CH_2Z,$$

a group $$COOR_{10}$$

(R$_{10}$ being an alkyl group of up to 6 carbon atoms); see, e.g., U.S. Pat. Nos. 3,824,260; 3,919,421; and 2,944,577, whose disclosures are incorporated by reference herein. One example of a corticoid of this structural class is fluocortine butyl ester. However, also suitable corticoids are those differing from the corticoids of Formula I by carrying a keto group in the 11-position. One example in this connection is clobetasone 17-butyrate.

The preparations of this invention usually contain 0.005–2% by weight and preferably 0.05–0.5% by weight of the corticoid(s); the concentration, of course, is dependent on the relative efficacy of the corticoid and can be routinely determined by fully conventional methods.

This invention furthermore relates to a process for the production of a corticoid-containing preparation in the form of an ointment, paste, cream, or the like, comprises producing, from a fatty phase, an aqueous phase, an oil/water emulsifier, and a preservative, an oil/water emulsion and, from a fatty phase, an aqueous phase, and a water/oil emulsifier, a water/oil emulsion; intimately intermixing by agitation the two emulsions with the addition of hydrophilic and/or lipophilic active ingredients under vacuum at a temperature of 20° to 40° C., and thereupon optionally combining the resultant, finely dispersed mixture with fragrance substances.

Even though, at first glance, it may appear obvious, in view of the various needs of the skin, to simply blend the two types of emulsion in order to produce a cream, to satisfy the hydrophilic/lipophilic needs of the skin, such a single mode of operation is not readily possible. This is so, because the two types of emulsion heretofore could not be stably maintained side-by-side; rather, in dependence on the components employed, a conversion of one type of emulsion into the other occurs, at least soon after processing, so that, in the final analysis, only one type of emulsion remains preserved in the thus-prepared cream.

The preparations of this invention are superior to those of the prior art in many ways. For example, according to DOS 19 49 740, it is allegedly necessary to add colloidal substances such as magnesium and aluminum silicate as layer-forming active ingredients. The preparations of this invention do not contain such potentially allergy-causing additives. Instead, the emulsions of the present invention are mixtures of water/oil and oil/water emulsions and therefore combine the properties of a fat-restoring formulation, e.g., cream and a normal formulation, e.g., cream. Accordingly, they are of very universal application. These effects are not suggested by the prior art, including the mentioned DOS. In addition, the preparations of this invention are surprisingly galenically stable. They also show lower side effects than known corticoid-containing preparations, e.g., lower allergic side effects, irritations, sensitivities, macerations, burning sensations and itching.

When the two types of emulsion are combined at temperatures of 20° to 40° C., preferably at about 30° C., under a vacuum in an agitated vessel in an especially gentle fashion, yet, notwithstanding this latter feature, in a very intensive manner, so that finally a very fine dispersion of the two emulsions is obtained wherein the particle size is 2 to 50 $\mu$m, preferably 5 to 15 $\mu$m, then the type types of emulsion will be retained unchanged in side-by-side relationship in the thus-prepared cream. Suitable stirrers which can be used include those which are fully conventional in the preparation of conventional salves, creams and the like.

Thus, "extremely finely dispersed" herein means particle sizes of 2–50 $\mu$m. This emulsion system remains stable even at a considerable dilution, for example with a liquid phase. It is assumed that significant factors for the stability of this emulsion system are the particle size as well as the collaboration of the emulsifiers. The essential point is that, in the preparation of the cosmetic of this invention, the emulsions utilized are dispersed rather than homogenized.

Combining the two emulsions takes place preferably under a vacuum of 0.5 torr to 50 torr. The agitation speed is dependent on the type of agitator, as is well-known to those skilled in the art, and must be determined in a manner known per se. In general, the preparations of this invention are fully conventional except for the combination of corticoid and jojoba oil, and all of the ingredients are fully conventional.

The oil/water emulsions and the water/oil emulsions can be produced conventionally with the use of known emulsifiers, (See, e.g., Kirk Othmer, Encyclopedia of Chemical Technology, 3rd ed., 1979; John Wiley and Sons, N.Y., etc., 8:900-930; and Dr. Otto-Albrecht Neumueller, "Roempp's Chemie Lexikon" [Roempp's Chemical Dictionary] 7th ed., 1973, Franckh'sche Verlagshandlung [publishers] Stuttgart, pp. 1009-1013; whose disclosures are incorporated by reference herein). The waxes, emulsifiers, and other additives utilized for these emulsions are the same as conventionally employed in emulsified skin-care agents. (See, e.g., Dr. Otto-Albrecht Neumueller, "Roempp's Chemie Lexikon" 7th ed., 1973, Franckh'sche Verlagshandlung Stuttgart, pp. 1427 and 1428, whose disclosure is incorporated by reference herein).

Oil/water emulsions useful in the preparations of this invention can comprise hydrophilic and/or lipophilic active agents, a fatty phase, an oil/water emulsifier, an aqueous phase, and a preservative, as is known.

Suitable hydrophilic and/or lipophilic active ingredients include moisturizing factors (hydrocomplexes), e.g., glycerol, polyethylene glycols, or amino acid mixtures, "Puroba" oil (=jojoba oil), vitamins (preferably vitamins A and E), vitalizing complexes (such as, for example, placenta extracts), enzymes, herbal extracts (e.g., hamamelis extract or camomile extract), or proteins (such as, for example, collagen). Suitable as the oily phase or fatty phase in the oil/water emulsions are hydrocarbons, such as, for example, "Vaseline," paraffins, or stearin, or waxes, e.g., beeswax. Suitable oil/water emulsifiers include, for example, stearyl alcohol, polyoxyethylene stearates (such as, for example, "Myrj"), complex emulsifiers (e.g., "Amphoterin"), and sorbitan fatty acid esters (such as, for example, "Span") or carboxyvinyl polymers (e.g., "Carbopol"). The aqueous phase can additionally contain buffers, such as, for example, the disodium salt of ethylenediamine-N,N,N',N'-tetraacetic acid, and preservatives, such as chlorquinaldol, "Parabens," or benzalkonium chloride.

In the oil/water emulsions, the proportion of the internal phase of the emulsion is preferably 30–49% by weight; the particle size of the internal emulsion preferably is 1 $\mu$m to 100 $\mu$m. During dispersing of the two phases, the particle size is once more diminished and ranges below 50 $\mu$m in the finished product.

Water/oil emulsions usable in the cosmetic agents of this invention again comprise hydrophilic and/or lipophilic active agents such as those utilized in the oil/water emulsion, a fatty phase, a water/oil emulsifier, and an aqueous phase. Suitable ingredients as the oily phase or fatty phase of the water/oil emulsion include hydrocarbons, e.g., paraffins and "Vaseline," synthetic, vegetable, and animal oils or waxes (e.g., olive oil, peanut oil, fine bone oil, almond oil, lanolin, beeswax, or sunflower oil); usable ingredients as the aqueous phase include purified demineralized water and, as the water/oil emulsifier, wool fat (=lanolin), fatty alcohols, e.g., cetyl alcohol, myristyl alcohol, stearyl alcohol, or ceryl alcohol, fatty acid esters, such as, for example, beeswax (Cera alba) or wax alcohol esters or mixed esters (such as, for example, "Dehymuls").

In the water/oil emulsions, the proportion of the internal phase of the emulsion is preferably 30–49% by weight; the particle size of the internal emulsion is preferably 1 $\mu$m to 100 $\mu$m. During the dispersion of the two phases, the size is once again diminished and, in the finished product, is preferably below 50 $\mu$m.

The mixture ratio of oil/water emulsion and water/oil emulsion is preferably 20–80% by weight, and in particular, 35–65% of oil/water emulsion. The finely dispersed system is additionally combined with the micronized corticoid (particle size preferably 1–20 $\mu$m) and, if desired, also with fragrance compounds, e.g., those of the "Crematest" series, and agitated until they are uniformly distributed.

Using the cream or other preparation containing the extremely finely dispersed mixture of the two types of emulsions, it is possible to produce an oil/water or water/oil hydrolipid film on a particular location of skin adapted to the particular moisture content of the latter over the varying areas of the skin and/or depending on the type of skin. Perhaps, a few routine preliminary experiments might be required to adapt the oil/water and water/oil details to this given application.

The corticoid-containing preparation of this invention in the form of a cream can have the following composition, for example:

|  |  | Tolerances |
|---|---|---|
| Hydrocortisone 21-acetate, micronized | 0.5% | 0.1–1% |

-continued

|  | | Tolerances |
|---|---|---|
| (particle size primarily 1–20 μm) | | |
| "Puroba" oil | 5% | 5–10% |
| Cera alba (beeswax) | 1% | 1–5% |
| "Dehymuls" | 1% | 1–3% |
| Stearyl alcohol | 4% | 4–8% |
| Hydrocarbons | 30% | 30–50% |
| "Carbopol" | 1% | |
| "Myrj" | 3% | 2–5% |
| Disodium edetate | 1% | |
| Chlorquinaldol | 1% | |
| Purified demineralized water | 52% | 30–55% |
| Perfume oil | 0.5% | |

The data are set forth in weight percent.

The process of this invention can be conducted using all devices conventionally employed for the preparation of ointments, creams, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of Oil/Water Emulsion 10.00 g of disodium edetate and 10.00 g of chlorquinaldol are dissolved in 300.00 g of purified demineralized water and combined with 10.00 g of "Carbopol".

This mixture is introduced under vigorous agitation into a melt of 80.00 g of "Vaseline" (DAB 8)—DAB being the abbreviation for the German Pharmacopoeia, official issue, 8th edition 1978—40.00 g of stearyl alcohol, 30.00 g of "Myrj", and 50.00 g of "Puroba" oil. The mixture is stirred until an emulsion is produced having a particle size of 20–70 μm.

Preparation of Water/Oil Emulsion 228.00 g of purified demineralized water is introduced under vigorous agitation into a melt of 220.00 g of "Vaseline" (DAB 8), 10.00 g of "Dehymuls", and 10.00 g of Cera alba. The mixture is agitated until an emulsion is produced having a particle size of 20–70 μm.

Preparation of a Cream

The water/oil emulsion is introduced under vigorous stirring and under a vacuum of 10 torr into the oil/water emulsion. The mixture is agitated until a dispersion is produced having a particle size of 10–50 μm; the vacuum is removed, 5.000 g of hydrocortisone 21-acetate-micronized, particle size primarily 1–20 μm, and 2.00 g of a fragrance compound of the "Crematest" series are added under agitation, and stirring is continued until both components have been uniformly distributed in the ointment base.

EXAMPLE 2

Preparation of Oil/Water Emulsion 10.00 g of disodium edetate and 10.00 g of chlorquinaldol are dissolved in 300.00 g of purified demineralized water and are combined with 10.00 g of "Carbopol".

This mixture is introduced under vigorous stirring into a melt of 80.00 g of "Vaseline" (DAB 8)—DAB being the abbreviation for the German Pharmacopoeia, official issue, 8th edition 1978—40.00 g of stearyl alcohol, 30.00 g of "Myrj", and 50.00 g of "Puroba" oil. The mixture is agitated until an emulsion is produced having a particle size of 20–70 μm.

Preparation of Water/Oil Emulsion 227.00 g of purified demineralized water is introduced under vigorous agitation into a melt of 220.00 g of "Vaseline" (DAB 8), 10.00 g of "Dehymuls", and 10.00 g of Cera alba. The mixture is stirred until an emulsion is formed having a particle size of 20–70 μm.

Preparation of a Cream

The water/oil emulsion is introduced under vigorous agitation and under a vacuum of 10 torr into the oil/water emulsion. The mixture is stirred until a dispersion is obtained having a particle size of 10–50 μm; the vacuum is removed; under agitation, 1.000 g of 21-acetoxy-11β-hydroxy-6α-methyl-17α-propionyloxy-1,4-pregnadiene-3,20-dione-micronized, particle size primarily 1–20 μm, and 2.00 g of a fragrance substance of "Crematest" are added to the mixture and the latter is stirred further until both components have been uniformly distributed in the ointment base.

EXAMPLE 3

Preparation of Oil/Water Emulsion 10.00 g of disodium edetate and 10.00 g of chlorquinaldol are dissolved in 300.00 g of purified demineralized water and combined with 10.00 g of "Carbopol".

This mixture is introduced under vigorous stirring into a melt of 80.00 g of "Vaseline" (DAB 8)—DAB being the abbreviation for the German Pharmacopoeia, official issue, 8th edition 1978—40.00 g of stearyl alcohol, 30.00 g of "Myrj", and 50.00 g of "Puroba" oil. The mixture is stirred until an emulsion is produced having a particle size of 20–70 μm.

Preparation of Water/Oil Emulsion 227.00 g of purified demineralized water is introduced under vigorous agitation into a melt of 220.00 g of "Vaseline" (DAB 8), 10.00 g of "Dehymuls", and 10.00 g of Cera alba. The mixture is stirred until an emulsion is formed having a particle size of 20–70 μm.

Preparation of a Cream

The water/oil emulsion is introduced under vigorous agitation and under a vacuum of 10 torr into the oil/water emulsion. The mixture is stirred until a dispersion is obtained having a particle size of 10–50 μm; the vacuum is removed; under agitation, 1.000 g of 21-acetoxy-17α-butyryloxy-11β-hydroxy-6α-methyl-4-pregnene-3,20-dione-micronized, particle size primarily 1–20 μm, and 2.00 g of a fragrance substance of "Crematest" are added to the mixture and the latter is stirred further until both components have been uniformly distributed in the ointment base.

EXAMPLE 4

Preparation of Oil/Water Emulsion 10.00 g of disodium edetate and 10.00 g of chlorquinaldol are dissolved in 300.00 g of purified demineralized water and combined with 10.00 g of "Carbopol".

This mixture is introduced under vigorous stirring into a melt of 80.00 g of "Vaseline" (DAB 8)—DAB being the abbreviation for the German Pharmacopoeia, official issue, 8th edition 1978—40.00 g of stearyl alcohol, 30.00 g of "Mryj", and 50.00 g of "Puroba" oil. The mixture is stirred until an emulsion is produced having a particle size of 20–70 $\mu$m.

Preparation of Water/Oil Emulsion 227.00 g of purified demineralized water is introduced under vigorous agitation into a melt of 220.00 g of "Vaseline" (DAB 8), 10.00 g of "Dehymuls", and 10.00 g of Cera alba. The mixture is stirred until an emulsion is formed having a particle size of 20–70 $\mu$m.

Preparation of a Cream

The water/oil emulsion is introduced under vigorous agitation and under a vacuum of 10 torr into the oil/water emulsion. The mixture is stirred until a dispersion is obtained having a particle size of 10–50 $\mu$m; the vacuum is removed; under agitation, 1.000 g of 21 acetoxy-9$\alpha$-choloro-11$\beta$-hydroxy-17$\alpha$-propionyloxy-1,4-pregnadiene-3,20-dione-micronized, particle size primarily 1–20 $\mu$m, and 2.00 g of a fragrance substance of "Creamatest" are added to the mixture and the latter is stirred further until both components have been uniformly distributed in the ointment base.

EXAMPLE 5

Preparation of Oil/Water Emulsion 10.00 g of disodium edetate and 10.00 g of chlorquinaldol are dissolved in 300.00 g of purified demineralized water and combined with 10.00 g of "Carbopol".

This mixture is introduced under vigorous stirring into a melt of 80.00 g of "Vaseline" (DAB 8)—DAB being the abbreviation for the German Pharmacopoeia, official issue, 8th edition 1978—40.00 g of stearyl alcohol, 30.00 g of "Myrj", and 50.00 g of "Puroba" oil. The mixture is stirred until an emulsion is produced having a particle size of 20–70 $\mu$m.

Preparation of Water/Oil Emulsion 227.50 g of purified demineralized water is introduced under vigorous agitation into a melt of 220.00 g of "Vaseline" (DAB 8), 10.00 g of "Dehymuls", and 10.00 g of Cera alba. The mixture is stirred until an emulsion is formed having a particle size of 20–70 $\mu$m.

Preparation of a Cream

The water/oil emulsion is introduced under vigorous agitation and under a vaccum of 10 torr into the oil/water emulsion. The mixture is stirred until a dispersion is obtained having a particle size of 10–50 $\mu$m; the vacuum is removed; under agitation, 0.500 g of clobetasol 17-propionate-micronized, particle size primarily 1–20 $\mu$m, and 2.00 g of a fragrance substance of "Crematest" are added to the mixture and the latter is stirred further until both components have been uniformly distributed in the ointment base.

EXAMPLE 6

Preparation of Oil/Water Emulsion 10.00 g of disodium edetate and 10.00 g of chlorquinaldol are dissolved in 300.00 g of purified demineralized water and combined with 10.00 g of "Carbopol".

This mixture is introduced under vigorous stirring into a melt of 80.00 g of "Vaseline" (DAB 8)—DAB being the abbreviation for the German Pharmacopcia, official issue, 8th edition 1978—40.00 g of stearyl alcohol, 30.00 g of "Myrj", and 50.00 g of "Puroba" oil. The mixture is stirred until an emulsion is produced having a particle size of 20–70 $\mu$m.

Preparation of Water/Oil Emulsion 227.00 g of purified demineralized water is introduced under vigorous agitation into a melt of 220.00 g of "Vaseline" (DAB 8), 10.00 g of "Dehymuls", a 10.00 g of Cera alba. The mixture is stirred until an emulsion is formed having a particle size of 20–70 $\mu$m.

Preparation of a Cream

The water/oil emulsion is introduced under vigorous agitation and under a vacuum of 10 torr into the oil/water emulsion. The mixture is stirred until a dispersion is obtained having a particle size of 10–50 $\mu$m; the vacuum is removed; under agitation, 1.000 g of diflucortolone 21-valerate-micronized, particle size primarily 1–20 $\mu$m, and 2.00 g of a fragrance substance of "Creamatest" are added to the mixture and the latter is further agitated until both components have been uniformly distributed in the ointment base.

EXAMPLE 7

Preparation of Oil/Water Emulsion 10.00 g of disodium edetate and 10.00 g of chlorquinaldol are dissolved in 300.00 g of purified demineralized water and combined with 10.00 g of "Carbopol".

This mixture is introduced under vigorous stirring into a melt of 80.00 g of "Vaseline" (DAB 8)—DAB being the abbreviation for the German Pharmacopoeia, official issue, 8th edition 1978—40.00 g of stearyl alcohol, 30.00 g of "Myrj", and 50.00 g of "Puroba" oil. The mixture i stirred until an emulsion is produced having a particle size of 20–70 $\mu$m.

Preparation of Water/Oil Emulsion 227.00 g of purified demineralized water is introduced under vigorous agitation into a melt of 220.00 g of "Vaseline" (DAB 8), 10.00 g of "Dehymuls", and 10.00 g of Cera alba. The mixture is stirred until an emulsion is formed having a particle size of 20–70 $\mu$m.

Preparation of a Cream

The water/oil emulsion is introduced under vigorous agitation and under a vacuum of 10 torr into the oil/water emulsion. The mixture is stirred until a dispersion is obtained having a particle size of 10–50 $\mu$m; the vacuum is removed; under agitation, 1.000 g of 21-acetoxy-17$\alpha$-ethoxy-methoxy-11$\beta$-hydroxy-1,4-pregnadiene-3,20-dione-micronized, particle size primarily 1–20 $\mu$m, and 2.00 g of a fragrance substance of "Crematest" are added to the mixture and the latter is further agitated until both components have been uniformly distributed in the ointment base.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a corticoid-containing pharmaceutical preparation adapted for topical application, comprising 0.005-2% by weight of a corticoid having anti-inflammatory activity, a fatty phase, an aqueous phase, and at least one emulsifier, the improvement wherein:
   the corticoid, the fatty acid, and the aqueous phase are present in the form of a stable dispersed mixture of (a) an oil/water emulsion containing an oil/water emulsifier, and (b) a water/oil emulsion containing a water/oil emulsifier, the particle size of the inner phase of the emulsions being 2–50 μm,
   said oil/water emulsion and water/oil emulsion are present in said stable dispersed mixture in a side-by-side relationship, and
   said preparation further contains jojoba oil.

2. A composition of claim 1, wherein the oil/water emulsion is prepared from the fatty phase, an aqueous phase, oil/water emulsifier, and preservative, and the water/oil emulsion is prepared from the fatty phase, aqueous phase, and water/oil emulsifier; the two emulsions are intimately intermixed with agitation, while adding hydrophilic and/or lipophilic active agents, under a vacuum at a temperature of about 20° to 40° C.; and then, combining the resultant, finely dispersed mixture with the corticoid in micronized form and with said fragrant substance.

3. A composition of claim 1 wherein the amount of corticoid is 0.05-0.5% by weight.

4. A composition of claim 1 wherein said particle size is 5–15 μm.

5. A composition of claim 1 wherein in the oil/water and water/oil emulsions the proportion of the internal phase is 30–49% by weight.

6. A composition of claim 1 wherein the amount of oil/water emulsion is 20–80% by weight and the proportion of water/oil emulsion is 80–20% by weight.

7. A composition of claim 1 wherein the particle size of the corticord is 1–20 μm.

8. In a method of administering a topical anti-inflammatory composition to a patient in need of such treatment, the improvement wherein the composition is that of claim 1.

9. A composition of claim 1, wherein said preparation contains 5–10 wt.% jojoba oil.

10. A composition of claim 1, wherein the corticoid is of the formula

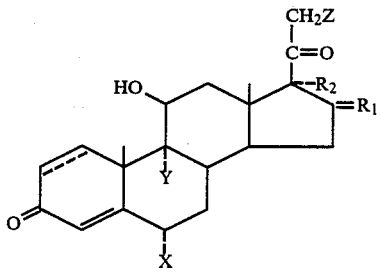

wherein is a single bond or a double bond,
X is hydrogen, fluorine, or methyl,
Y is hydrogen, fluorine, or chlorine,
Z is hydroxy, alkanoyloxy of 2–6 carbon atoms, benzoyloxy, or chlorine,
$R_1$ and $R_2$ jointly represent an isopropylidenedioxy group, or
$R_1$ is two hydrogen atoms, a hydrogen atom and a methyl group, and
$R_2$ is hydrogen, hydroxy, alkanoyloxy of 2–6 carbon atoms, ($C_{1-4}$-alkoxy)methyl, or benzoloxy.

11. A composition of claim 10 wherein the corticoid is of the formula

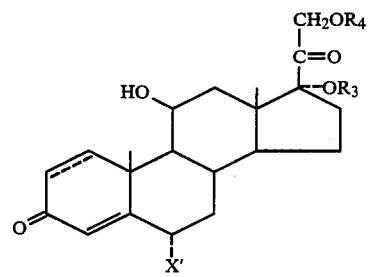

wherein is a single bond or a double bond,
X' is hydrogen or methyl, and
$R_3$ and $R_4$, being identical or different, are hydrogen, alkanoyl of 2–6 carbon atoms, ($C_{1-4}$-alkoxy)-methyl, or benzoyl.

12. A composition of claim 10 wherein the corticoid is of the formula

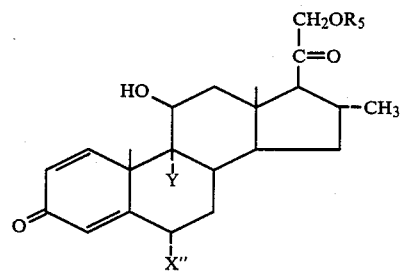

wherein
Y is as defined in claim 2,
X" is hydrogen or fluorine, and
$R_5$ is hydrogen, alkanoyl of 2–6 carbon atoms, or benzoyl.

13. A composition of claim 10, wherein the corticoid is of the formula

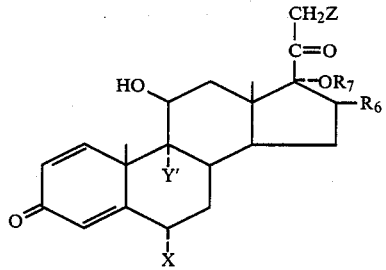

wherein
X and Z are as defined in claim 2,
$R_6$ is hydrogen, methylene, or methyl and $R_7$ is hydrogen, alkanoyl of 2-6 carbon atoms, or benzoyl.

14. A composition of claim 10 wherein the corticoid is of the formula

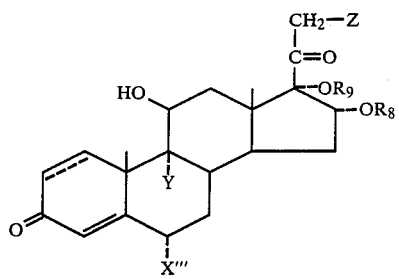

wherein ---Z, and Y are as defined in claim 2,
X''' is hydrogen or fluorine, and
$R_8$ and $R_9$ each represents hydrogen or collectively they represent isopropylidene.

15. A composition of claim 10, wherein said fragrant substance is a compound selected from the Crematest series.

* * * * *

UNITED STATES PATENT AND TRADEMARK OFFICE
CERTIFICATE OF CORRECTION

PATENT NO. : 4,918,065
DATED : April 17, 1990
INVENTOR(S) : Wolfgang Stindl et al It is certified that error appears in the above-identified patent and that said Letters Patent is hereby corrected as shown below:

Column 12, claim 10, line 1:

reads "wherein is a single bond or a double bond,"

should read -- wherein ---- is a single bond or a double bond, --

Column 12, claim 10, lines 8 and 9:

reads "$R_1$ is two hydrogen atoms, a hydrogen atom and a methyl group, and"

should read -- $R_1$ is two hydrogen atoms, a hydrogen atom and a hydroxy group a methylene group, or a hydrogen atom and a methyl group, and Column 12, claim 11, line 27:

reads "wherein is a single bond or a double bond,"

should read -- wherein ---- is a single bond or a double bond, --

Signed and Sealed this

Thirtieth Day of July, 1991

*Attest:*

HARRY F. MANBECK, JR.

*Attesting Officer*      *Commissioner of Patents and Trademarks*